(12) United States Patent
Tian

(10) Patent No.: US 8,334,141 B2
(45) Date of Patent: Dec. 18, 2012

(54) HYDRATE INHIBITION TEST LOOP

(75) Inventor: Jun Tian, League City, TX (US)

(73) Assignee: Baker Hughes Incorporated, Houston, TX (US)

( * ) Notice: Subject to any disclaimer, the term of this patent is extended or adjusted under 35 U.S.C. 154(b) by 0 days.

(21) Appl. No.: 12/897,557

(22) Filed: Oct. 4, 2010

(65) Prior Publication Data

US 2011/0081729 A1  Apr. 7, 2011

Related U.S. Application Data

(63) Continuation-in-part of application No. 11/969,115, filed on Jan. 3, 2008, now abandoned.

(51) Int. Cl.
*G01N 33/00* (2006.01)
*B01J 19/00* (2006.01)

(52) U.S. Cl. ....... 436/127; 436/106; 436/119; 422/68.1; 422/50

(58) Field of Classification Search ............. 422/68.1, 422/50; 423/262, 351; 436/106, 119, 127
See application file for complete search history.

(56) References Cited

U.S. PATENT DOCUMENTS

| | | | |
|---|---|---|---|
| 3,673,629 A | 7/1972 | Casey et al. | |
| 5,020,561 A * | 6/1991 | Li | 137/13 |
| 6,222,083 B1 | 4/2001 | Colle | |
| 6,628,118 B1 | 9/2003 | Amini | |
| 6,962,199 B1 | 11/2005 | Tjeenk Willink | |
| 2007/0276169 A1 | 11/2007 | Tohidi et al. | |
| 2009/0175774 A1 | 7/2009 | Tian | |

FOREIGN PATENT DOCUMENTS

WO  2008056252 A2  5/2008

OTHER PUBLICATIONS

Urdahl, O. et al., "Inhibition of Gas Hydrate Formation by Means of Chemical Additives—I. Development of an Experimental Set Up for Characterization of Gas Hydrate Inhibitor Efficiency With Respect to Flow Properties and Deposition." Chem. Engr Science, vol. 50, No. 5. pp. 863-870 (1995).
Lund, A. et al., "Inhibition of Gas Hydrate Formation by Means of Chemical Additives—II. An Evaluation of the Screening Method," Chem. Engr Science, vol. 51, No. 13, pp. 3449-3458 (1996).

* cited by examiner

*Primary Examiner* — Christine T Mui
(74) *Attorney, Agent, or Firm* — Mossman Kumar & Tyler PC

(57) ABSTRACT

The detecting and monitoring of solid structure or phase transformation, such as those used for testing the formation of gas hydrates and their inhibition by chemical additives may be conducted in a multi-test assembly of laboratory bench scale loops. The test loop contains a fluid that includes water and hydrate-forming guest molecules such as methane, ethane, carbon dioxide and the like at hydrate-forming conditions of low temperature and high pressure. A small bit or "pig" may be circulated through the test loop at variable speeds to circulate the fluid in the loop. The pig may be moved or impelled through the test loop remotely. The exterior of the pig and/or the interior of the loop may be smooth and/or have a friction-reducing coating thereon to facilitate movement of the pig through the loop. The formation of hydrates may be monitored with consistent and reproducible results.

22 Claims, 2 Drawing Sheets

HYDRATE INHIBITION TEST LOOP

CROSS-REFERENCE TO RELATED APPLICATION

This application is a continuation-in-part application of U.S. patent application Ser. No. 11/969,115, filed on Jan. 3, 2008.

TECHNICAL FIELD

The invention relates to methods and apparatus for a multi-test assembly for the detecting and monitoring solid structure formation or phase transformation, such as those used for testing the formation and inhibition of hydrocarbon hydrates, and most particularly relates, in one non-limiting embodiment, to methods and apparatus for testing the formation and inhibition optimization of hydrocarbon hydrates in a consistent, reproducible manner on a laboratory bench and pilot scale. The multi-test assembly can have built-in systems for pressure and temperature control.

BACKGROUND

A number of hydrocarbons, especially lower-boiling light hydrocarbons, in formation fluids or natural gas are known to form hydrates in conjunction with the water present in the system under a variety of conditions—particularly at a combination of lower temperature and higher pressure. The hydrates usually exist in solid forms that are essentially insoluble in the fluid itself. As a result, any solids in a formation or natural gas fluid are at least a nuisance for production, handling and transport of these fluids. It is not uncommon for hydrate solids (or crystals) to cause plugging and/or blockage of pipelines or transfer lines or other conduits, valves and/or safety devices and/or other equipment, resulting in shutdown, loss of production and risk of explosion or unintended release of hydrocarbons into the environment either on-land or off-shore. Accordingly, hydrocarbon hydrates have been of substantial interest as well as concern to many industries, particularly the petroleum and natural gas industries.

Hydrocarbon hydrates are clathrates, and are also referred to as inclusion compounds. Clathrates are cage structures formed between a host molecule and a guest molecule. A hydrocarbon hydrate generally is composed of crystals formed by water host molecules surrounding the hydrocarbon guest molecules. The smaller or lower-boiling hydrocarbon molecules, particularly $C_1$ (methane) to $C_4$ hydrocarbons and their mixtures, are more problematic because it is believed that their hydrate or clathrate crystals are easier to form. For instance, it is possible for ethane to form hydrates at as high as 4° C. at a pressure of about 1 MPa. If the pressure is about 3 MPa, ethane hydrates can form at as high a temperature as 14° C. Even certain non-hydrocarbons such as carbon dioxide, nitrogen and hydrogen sulfide are known to form hydrates under the proper conditions.

There are two broad chemical techniques to overcome or control the hydrocarbon hydrate flow hazards, namely thermodynamic and kinetic. The thermodynamic approach is to prevent hydrate formation by addition of "antifreeze" to the production fluids. The kinetic approach generally attempts (a) to prevent the smaller hydrocarbon hydrate crystals from agglomerating into larger ones (known in the industry as an anti-agglomerate and abbreviated AA) and/or (b) to inhibit, retard and/or prevent initial hydrocarbon hydrate crystal nucleation; and/or crystal growth (known in the industry as a kinetic hydrate inhibitor and abbreviated KHI). Thermodynamic and kinetic hydrate control methods may be used in conjunction.

Kinetic efforts to control hydrates have included the use of different materials as inhibitors. For instance, onium compounds with at least four carbon substituents are used as AA to inhibit the plugging of conduits by gas hydrates. Additives such as polymers with lactam rings have also been employed as KHI to control clathrate hydrates in fluid systems. All these kinetic inhibitors are commonly labeled as Low Dosage Hydrate Inhibitors (LDHI) in the art. KHIs and even LDHIs are relatively expensive materials, and it is always advantageous to determine ways of lowering the usage levels of these hydrate inhibitors while maintaining effective hydrate inhibition.

In order to identify and evaluate potential hydrate inhibitors and appropriate dosages or concentrations, a number of bench testing methods have been used, including rocking cells, autoclaves and wheels. One gas hydrate test apparatus includes a bank of pressurized sight glass cells, typically sapphire, each cell containing two stainless steel balls and a pressure transducer. In a typical experiment, each cell is either rocked (to simulate flow conditions) or held static (to simulate a shut-in condition) during the course of each experiment. The rocking motion, when employed, causes the stainless steel balls within the cells to traverse each cell's longitudinal axis, creating additional agitation. During shut-in simulations, the cells are placed at a horizontal stagnant position. Data logging includes monitoring the water bath temperature, the pressure of each cell and periodic visual observations. As all experiments are isochoric, the cell pressure decreases as the cell temperature is lowered. A maximum cell working pressure at room temperature may be about 1500 psig (10.3 MPa). A typical maximum test pressure at 40° F. (4.4° C.) may be between about 1100 psig (7.6 MPa) and 1350 psig (9.3 MPa).

Visual observations include documenting a rating assessment of the cell's contents: a determination if hydrates are visible, an evaluation of any visible hydrate's surface adhesion properties, and an estimate of liquid levels. A "pass" is typically rated as an "A", "B" or "C". A "pass" is judged when no hydrates form, or if hydrates do form, the crystals remain small (usually barely visible), the crystals do not agglomerate, the crystals do not adhere to any surfaces, and/or fluid viscosities remain low. A "fail" rating is given ("D" or "F") if the hydrates form plugs or deposits and/or fluid viscosities increase significantly.

Quality control for KHIs is achieved by performing controlled blank experiments with no hydrate inhibitor present in the system. Moreover, a statistical analysis on induction times of repeat runs also provides a measure of variation. From time to time it has been found that these methods are not very repeatable or consistent, especially when multiphase occurring in the system. The best minimum relative standard deviation (RSD) for rocking cells and autoclave methods is at least 25.

A similar experience has also been encountered in autoclave testing. Autoclave testing involves a high pressure stirred cell that is also filled with brine, gas and condensate or oil. The autoclave may have a sight glass. The cell is placed in a jacket or immersed in a temperature controlled bath. The cell is slowly cooled or quench cooled and held at either constant pressure or constant volume. The inner temperature is monitored, and the contents and viscosity are visually monitored, such as by image monitoring, and the torque on the stirrer is measured.

Wheel apparatus, such as wheel-shaped pipe flow loops licensed by Sintef, may consist of 2- to 5-inch (5.1- to 12.7 cm) pipe, shaped as a circular loop or wheel of 2 meters in diameter that rotates about a horizontal axis. The speed that the wheel rotates determines the flow regime. Peripheral velocities may range from 0.3 to 5 m/s. No pumps or compressors are used. Pressures up to 250 bar (25 MPa) may be applied. The wheel may have at least one high pressure window, often two, that is observed with a video camera. As with the other methods, the wheel is filled with brine, gas and condensate or oil. The wheel is placed in a temperature-controlled chamber. The temperature may range from −10 to 90° C. The pressure, temperature, visual appearance and torque may all be monitored.

Conventional flow loops often comprise a stainless steel loop, usually with a sight glass for image recording. A pump provides circulation and the speed of the pump controls the flow regime. Sizes of flow loops range from bench scales of 0.5 inches (1.3 cm) in diameter to 10 feet long (3 m) up to pilot scales of 4 inches (10.2 cm) in diameter and 275 feet (84 m) long. The flow loops may be filled with brine, gas and condensate or oil. They may be closed systems or at constant pressure. The loop is typically placed in a temperature-controlled chamber or bath. Monitoring is done of the visual appearance, the temperature, the pressure, the pressure drop and/or water conversion. Flow loop reactor testing results are very repeatable. However, even the bench scale experimental apparatus are quite expensive. Each experimental run is typically very time consuming, requires considerable amounts of fluid, and a long lead time. In situations where evaluation of an approach or method to inhibit gas hydrates must occur quickly with limited field fluids, such apparatus are at a disadvantage.

Thus, it is desirable that new apparatus and methods of forming gas hydrate and its inhibition be found which would yield predictable and reliable test results and provide a consistent method for hydrate formation and inhibition testing. Such apparatus and method may ideally be relatively low cost, be easy to set up, be conducted in a relatively short time, and require minimum amounts of fluids.

SUMMARY

There is provided, in one form, a test apparatus for the formation of hydrates that includes a length of hollow pipe forming a loop, where the loop has an interior surface, and at least one opening in the loop. The test apparatus includes a cooler for cooling a fluid in the loop and a pressurizer for pressurizing the fluid in the loop. The test apparatus also includes at least one pig within the loop, where the pig has an exterior surface and at least one impeller adjacent to the loop that remotely impels the pig to circulate the loop with the fluid. In one non-limiting embodiment, the impeller is a magnet that tracks close to the loop and impels a small sphere or ball to travel inside the pipe. The loop interior surface and/or the pig exterior surface are smooth to facilitate and make it easier for the pig to travel through the loop.

In another non-limiting embodiment herein, there is provided a method of testing the formation of hydrates in a test apparatus such as that described immediately above. The method involves introducing a fluid into the hollow pipe of the loop through the opening, where the fluid includes water and hydrate-forming guest molecules that form hydrates at hydrate forming conditions. The fluid is cooled to a temperature of about 30° F. (−1° C.) or below and the fluid pressurized to a pressure of about 1000 psig (7 MPa) or above to create hydrate forming conditions. The pig is circulated through the loop using the impeller, and the fluid is monitored for hydrate formation. Again, the interior surface of the loop and/or the exterior surface of the pig are smooth.

DETAILED DESCRIPTION

Figure 1:
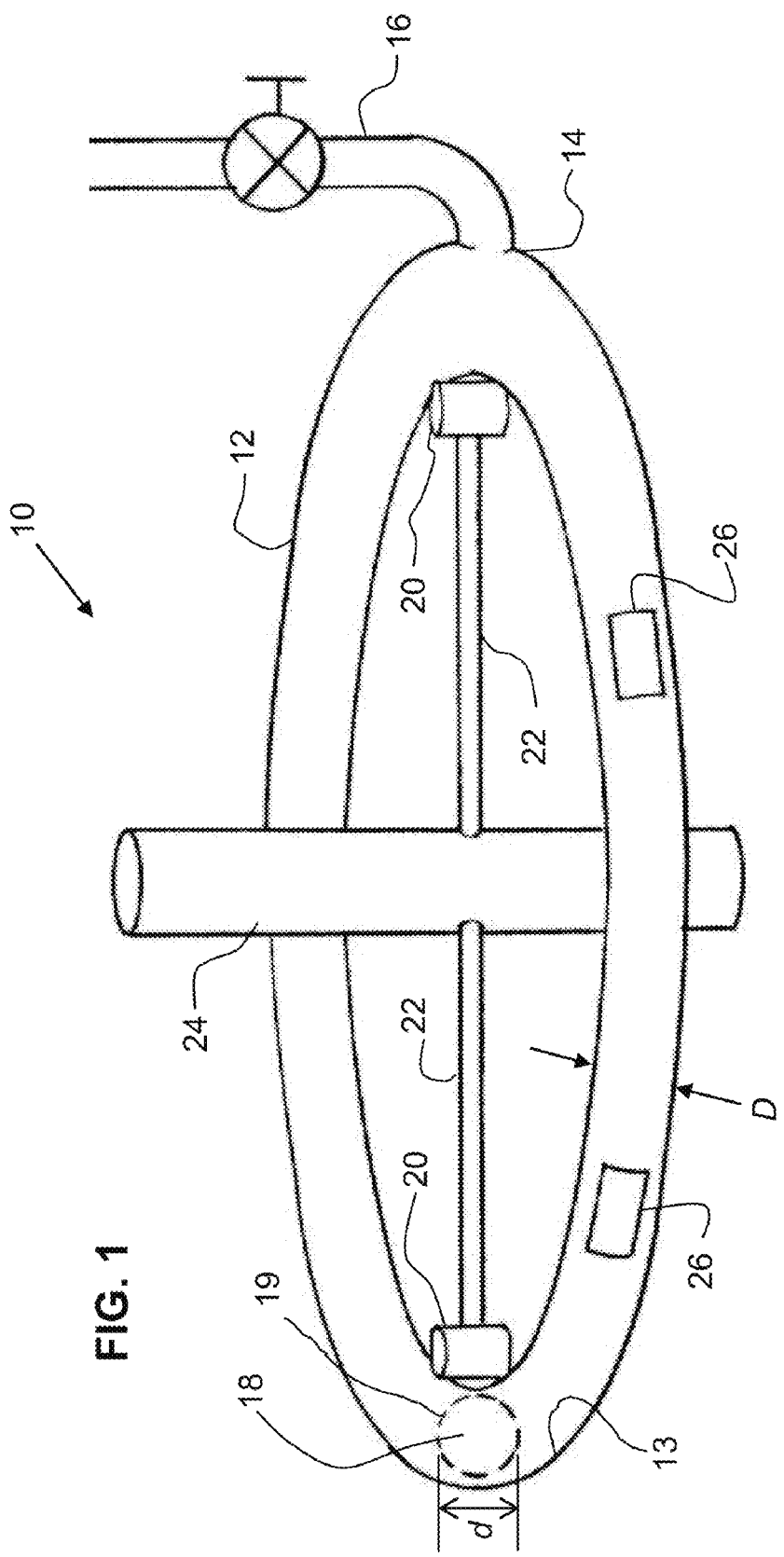
FIG. 1 is a schematic illustration of one embodiment of the test apparatus showing one loop having an opening therein and feed line connected thereto, where an impeller bearing a magnet impels a small "pig" or agitator to travel inside the loop.

As previously described, it has been found that prior methods of studying the intentional formation of hydrates, for instance gas hydrates, and methods of inhibiting their formation, tend to suffer from inconsistencies and not being repeatable. A method for laboratory bench hydrocarbon hydrate inhibition testing using a loop reactor has been discovered which involves contacting a fluid including a mixture of water and hydrate-forming guest molecules at gas hydrate forming conditions with an amount of inhibitor, such as a LDHI. In particular, it has been found that multiple tests may be run simultaneously for detecting and monitoring solid structure formation or phase transformations such as those occurring at the onset of and during hydrate formation. The multi-test apparatus may be used to help optimize inhibitors for hydrates, and may be used on a laboratory bench scale or pilot scale.

The bench scale test loop apparatus has been designed for determining the formation of hydrates in gas-liquid mixtures under different shearing conditions in a simulated flowing environment. As previously described, hydrates are crystalline solids formed under high pressure and low temperatures between hydrocarbon gases, such as methane, ethane, and the like, and water. Conventional high pressure test cells that employ a rocking motion to provide mixing from the motion of a steel ball have been criticized as not being representative enough of actual flowing pipeline conditions. Various other approaches have used large loops with pumps to circulate fluid, or even spinning the entire loop itself, but these methods have disadvantages including, but not limited to, expensive equipment requirements, long test set-up times, long test times, and/or large field liquid volume requirements.

The apparatus described herein has several unique aspects. The test loops may be quite small, in one non-limiting instance, a one-inch (2.54 cm) pipe formed into a 10-inch (25.4 cm) diameter test ring or loop. Multiple rings may be stacked around a central core, which contains a rotating head or impeller that pulls at least one spherical TEFLON®-coated ball (in one non-restrictive example) around the inside of each ring. Such a spinning, magnetically-equipped drive may be capable of relatively high speeds, in one non-restrictive example on the order of 3000 rpm, equaling 1.2 m/sec. The apparatus has proven to be quite steady and reliable. The entire assembly may be placed in a chilled bath and run at proven pressures of up to 2875 psig (19.8 MPa) or higher. Hydrate formation may be detected by monitoring the pressure in each ring with a transducer.

The use of a magnetic drive to yield a simulated loop flow in a hydrate test cell is novel and unique. Test results have proven to be quite consistent and reproducible. The apparatus enables testing in conditions that are not achievable using conventional rocking cells, and does not require the complexity of large state-of-the-art circulation loops. Moreover, operating multiple test loops or multi-testing can be achieved simultaneously under the same conditions.

The mechanism or force for driving the circulating balls, small-scale "pigs" or "bits" is not limited to magnetic force, and may be any proximity force or mechanism to generate different flow regimes inside a circulated loop by controlling the speed and shape of the bits, balls or "pigs". For instance, the surface of the circular pipe or loop may be substantially covered by an electromagnetic coil which is configured to generate a magnetic pulse around the loop at high speed that impels or propels the ball, bit or pig through the interior of the loop. In such a version the ball, bit or pig would not necessarily contact or touch the inner wall of the test loop except occasionally or when at rest. In another non-limiting embodiment, the ball, bit, or pig may be formed at least partially of a magnetic material such that it may be repelled or repulsed by a magnetic field generated in a an electromagnetic coil surrounding the interior or exterior surface of the loop; i.e. responsive to a magnetic field. The electromagnetic coil may be operated such that motion may be induced in the bit, ball, or pig along the path of the loop while the coil repels the ball, bit, or pig from the interior surface of the loop. It is expected that in this embodiment the ball, bit or pig will not contact the interior surface of the loop while it is being circulated, or would rarely contact the interior surface, since the ball, bit or pig would be repulsed in all directions from the interior surface of the loop.

In another non-limiting embodiment, the fluid may be pumped around the test loop at high speed, driving the pig, ball or bit along with it. Obviously, a conventional pump would not be suitable since the ball, bit or pig would interfere with and/or get caught in the vanes of the pump impeller. However, a pump having a hollow core coaxial with the pipe loop where the vanes are inset within the walls of the loop may be envisioned such that the fluid is propelled by the vanes, but the ball, bit or pig passes through the hollow core of the impeller. An alternative arrangement would be to withdraw fluid from the pipe loop through orifices relatively much smaller than the size of the ball, bit or pig, draw the fluid into a conventional pump and pump it back into the flow loop at a different location through other relatively small orifices or holes.

Shown in FIG. 1 is a schematic illustration of the apparatus 10 herein having a length of hollow pipe forming a loop 12, the loop 12 having an interior surface 13, where there is at least one opening 14 in the wall of the loop 12. Opening 14 may be connected to a pipe 16 which may be used to introduce or withdraw the fluid from the loop 12 or both. In one expected embodiment, there may be two openings in loop 12, each connected to its own pipe 16 or line, where fluid is introduced via one pipe and opening, and then withdrawn through another pipe or opening. Loop 12 may also be provided with a further opening, door or other orifice for introducing and/or removing the ball, bit or pig 18 into and from the loop 12. Ball, bit or pig 18 has an exterior surface 19, and the pig 18 may, in one non-limiting embodiment, be a TEFLON®-coated ferrous metal alloy sphere, although it will be understood that other low friction or non-stick coating materials may be used. The entire apparatus 10 may be place in or introduced into a cooler, heat exchanger or refrigeration unit to cool the fluid placed in the loop 12 to low temperatures, and may be pressurized by a pump, compressor or other pressurizer or pressurizing device to relative high temperatures, all to simulate hydrate-forming conditions. In one non-limiting embodiment the impeller to drive the ball, bit or pig 18 is a magnet 20 mounted on an armature 22, in turn attached to drive shaft 24. Magnet 20 is designed to be spun just inside the inner diameter of loop 12 to be sufficiently close to ball, pig or bit 18 to influence the latter to circulate in a fluid placed in the loop 12. In other words, the magnetic field emanating from magnet 20 being spun around the axis of drive shaft 24 while attached to armature 22 extends sufficiently into the interior of the loop 12 to compel the bit, ball or pig 18 to travel at the same revolutions per minute as the armature. For balance, it is expected that in most non-limiting embodiments, the drive shaft 24 will bear an essentially identical armature 22 on each side with an essentially identical magnet 20 or at least equivalent mass at the end thereof. If each armature 22 has a magnet 20, it would be possible, although in some cases not necessary, for the loop to contain a total of two bits, balls or pigs 18, one for each magnet.

Figure 2:
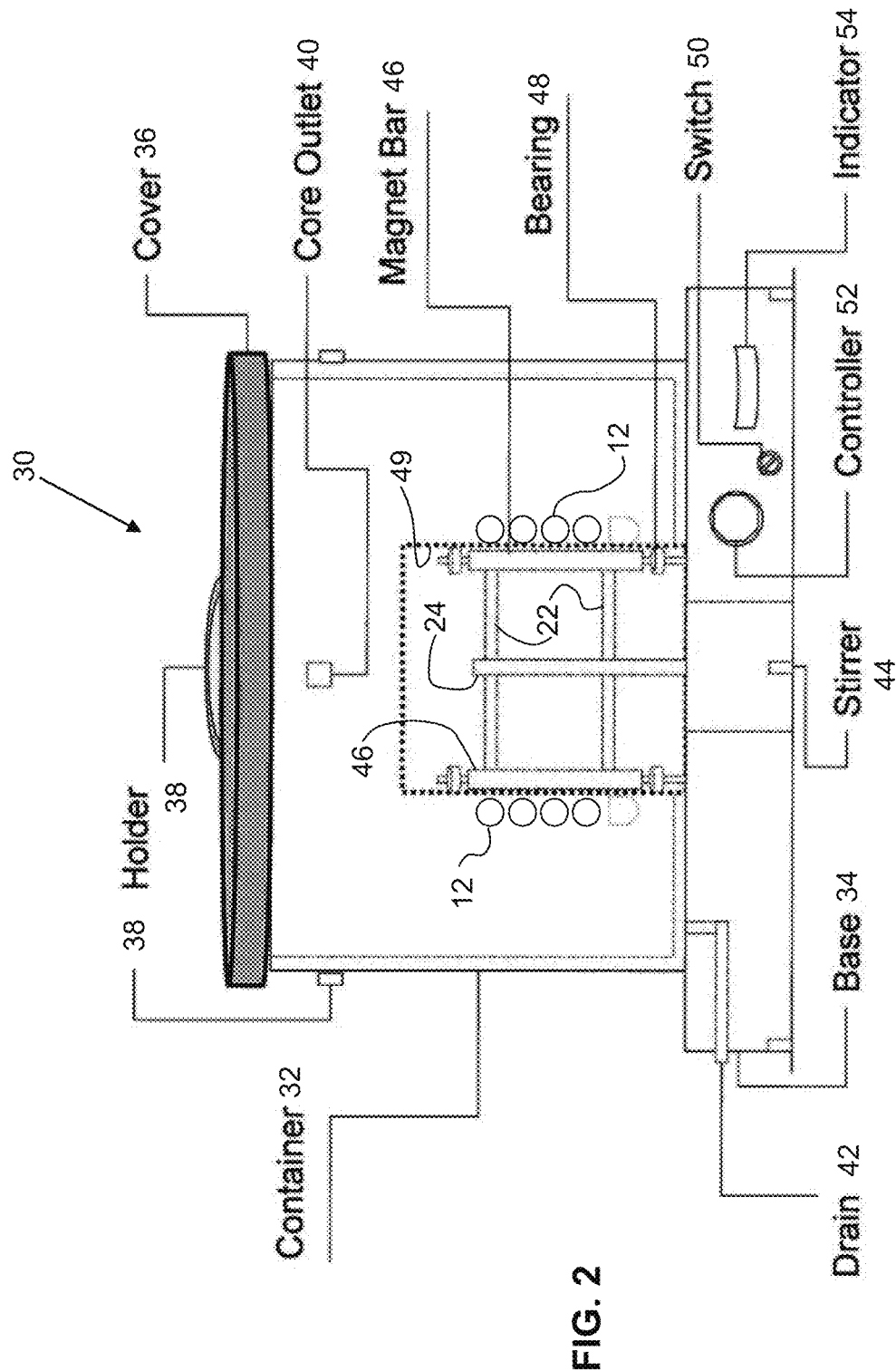
FIG. 2 is a schematic cross-section illustration of another embodiment of the test apparatus showing features and elements outside those shown in FIG. 1.

It will be understood that in the embodiments shown in FIGS. 1 and 2 that the "pig", bit or ball 18 is moving along the closed loop 12 within the fluid, instead of moving the fluid. It will also be understood that the shape of the closed loop 12 will conveniently be a circle when a rotating magnet 20 is the impeller, but the apparatus 10 is not limited to this shape. Other shapes for the loop 12 may be employed as long as the pig, bit or ball 18 may be impelled to move smoothly and quickly with loop 12.

However, it will also be appreciated that there could be only one or possibly many armatures 22 and magnets 24, and a bit, ball or pig 18 for each. With the addition of each ball, pig or bit 18 the flow dynamics in the loop 12 would change, and they would change also as the speed of the ball, bit or pig 18 would change. Other shapes of the ball, bit or pig 18 may be used besides spherical, for instance egg-shaped or short cylinders. The exterior surface 19 of the pig, ball or bit 18 may include but not be limited to, indentations such as dimples (similar to a golf ball), pits, grooves, and other depressions; raised features such as texturing, bumps and other concave areas; holes, orifices, and other openings, and the like. All of these changes would generate different flow regimes, flow patterns, turbulence or other flow dynamics inside the pipe 12, and are within the scope of the apparatus and methods described herein.

The pig, ball or bit 18 should not scrape against the interior surface or wall 13 of the loop 12; that is, there is an absence of scraping between the pig 18 and the interior surface or wall 13 of loop 12. Rolling of the pig, ball or bit 18 against the interior surface 13 and occasional touching of the pig, ball or bit 18 against the interior surface 13 is acceptable. As noted, the pig, ball or bit 18 is to generate flow, flow patterns, turbulence and other flow dynamics in the fluid within the loop; that is, generally circulate fluid within the loop 12. The pig, ball or bit 18 is not to scrape against the interior surface 13, for instance to scrape solids, such as hydrates, from the interior surface 13. To this end, the interior surface 13 and/or the exterior surface 19 of the pig, ball or bit 18 should be smooth. Smooth is defined as a texture that lacks or has reduced friction; not rough. In one non-limiting embodiment one or both of these surfaces is polished. In a non-limiting example, the surfaces may be polished stainless steel. The surfaces may be defined as "non-scraping" or "friction-reducing".

In another non-limiting embodiment, the interior surface or wall 13 of the loop 12 and/or the exterior surface 19 of the pig, ball or bit 18 may be coated with a non-stick or friction-reducing coating. Suitable friction-reducing coatings include, but are not necessarily limited to, the aforementioned TEFLON (polytetrafluoroethylene), fluorocarbons generally, silicone coatings, and the like.

Alternatively, or in addition to the above approaches, the loop 12 has an interior diameter (inside the hollow pipe; not to be confused with the inner diameter of loop 12) and the pig, ball or bit 18 has an exterior diameter. The exterior diameter of the pig 18 is smaller than the interior diameter of the respective loop 12 within which the pig 18 circulates. The difference in diameters is effective so that the exterior surface 19 of pig 18 does not scrape or abrade against the interior surface 13 of loop 12. In one non-limiting embodiment, the average clearance of the exterior surface 19 with respect to interior surface 13 is about 1 mm or more; in another non-restrictive version is about 2 mm or more alternatively is 2.5 mm or more. If the interior diameter of the loop 12 is D and the pig 18 exterior diameter is d, then d/D is less than 1. Stated another way, in another non-limiting embodiment, d is at least about 25% of D, alternatively d is at least 50% of D, and in another non-limiting embodiment d is at least 75% of D, but in all cases d/D<1.

In another, alternative approach, which may be used together with or instead of those discussed above, is to introduce an additive to the fluid within the loop to reduce scraping or friction as the pig 18 circulates or travels within loop 12. Suitable additives include, but are not necessarily limited to, high molecular weight silicone oils, for instance those having a viscosity of about 100,000 cps to about 600,000 cps. Such additives may be useful up to about 5 vol %, based on the total fluid, alternatively up to about 2 vol %, and in another non-limiting embodiment, up to about 1 vol %. In one non-limiting embodiment the weight average molecular weight of these silicone oils, Mw, may be about 90,000 or more.

One notable feature of the apparatus is that the loop 12 may be easily loaded and drained with liquids and gases through opening 14 and pipe 16 in the loop 12. It will be appreciated that the opening 14 and pipe 16 do not necessarily have to be located on the outer diameter of the loop 12, but may be located on the inner diameter, or on the top and/or bottom of the loop 12. Of course, if an impeller is a magnet 20 mounted on an armature 22 of the drive shaft 24 as shown in the configuration in FIG. 1, opening 14 and pipe 16 should not interfere with the path of magnet 20. However, magnet 20 need not rotate within the inner diameter of loop 12, but could also be configured to orbit around the outer diameter of loop 12, or just above or just below loop 12 in a different plane from that of loop 12 (the FIG. 1 configuration having the armature 22 and magnet 20 revolving in the same plane of loop 12). In each particular configuration, opening 14 and pipe 16 would need to be positioned so as not to interfere with the rotation.

It will be appreciated that shut-in conditions may be simulated simply by not impelling the bit, pig or ball 16 to move within test loop 12.

In one non-limiting embodiment of the apparatus herein, loop 12 may have one or more sight glasses 26 in the sides thereof to visually monitor the condition of the fluid therein. In such an apparatus, the pressure of the fluid may be on the order of 1500 psig (10.3 MPa). In other optional embodiments where higher pressures are used, such as 3000 psig (20.7 MPa) in a non-limiting embodiment, the flow loop 12 may not tolerate sight glasses therein.

Shown in FIG. 2 is a cross-sectional schematic illustration of another embodiment of the test apparatus herein. Apparatus 30 would be housed in a container 32 resting on a base 34, where the container 32 had a cover 36. Container 32 and cover 36 may be supplied with handles or holders 38. Container 32 may be equipped with a core outlet 40 for pressure transducer output and coolant circulation and a drain 42, for draining the contents of the container 32.

In the particular embodiment shown in FIG. 2, there are four loops 12 in a vertical stack, each having at least one opening 14 and pipe or line 16 (not shown) in communication therewith to introduce liquid to and/or from their respective loops 12.

In some non-limiting embodiments, one pipe or line 16 could supply all of the loops 12, with valves shutting off each respective loop. With such a structure, each loop 12 could be filled with the same fluid or with different fluids. The number of loops 12 in a stack is a matter of design choice, and may be more or less than the four shown in FIG. 2. Stirrer 44 is the motor or motive force driving or spinning drive shaft 24 to which armatures 22 are affixed, which bear magnet bars 46 as they spin within loops 12 on bearings 48. In the particular embodiment shown in FIG. 2, bearings or wheels 48 rotate on an inner wall 49 inside of the test loops 12 to help keep magnet bars 46 revolving smoothly and at a constant distance from test loops 12. Stirrer 44 would be turned on and off by switch 50 and its speed controlled by controller 52. Indicator 54 would display Rpm of the magnet bars 46.

Loops 12 may be supported within container 32 by any suitable rack or frame, and may be surrounded by a single long cooling coil (In one non-limiting example, ⅜-inch (0.95 cm) diameter stainless steel tubing of 60 feet (18.3 m) in length, or a plurality of cooling coils or other heat exchange structure or cooler to cool down the interior of container 32.)

Loops 12 may be pressurized by any suitable pressurizer, compressor or pressurizing device, including, but not limited to a pump and/or a booster. The multi-test assembly may have built-in systems for pressure and temperature control.

A prototype structure has been built with excellent control. Temperature calibrations were conducted using two different locations inside the cooling bath and it was found that bath temperature was very consistent and linear. Similarly, the rotation calibrations (rpm) and pressure calibrations were in tight, predictable ranges. It will be appreciated that in an embodiment such as that seen in FIG. 2 having multiple loops 12 that multiple tests may be carried out simultaneously as a single magnet bar 46 may drive pigs, balls or bits in more than one test loop 12 at the same time. This simultaneous testing saves considerable time.

The prototype apparatus has been used to study hydrate formation and hydrates have been successfully formed. When baseline conditions for the initiation of hydrate formation have been established the apparatus and methods herein may be used to determine if chemical hydrate inhibition candidates (either AA or LDHI chemicals or both) are effective and at what dosage under different sub-coolings.

Using the apparatus and methods described herein, methods and compositions may be discovered for inhibiting, retarding, mitigating, reducing, controlling and/or delaying formation of hydrocarbon hydrates or agglomerates of hydrates in various fluids, such as those used in hydrocarbon recovery operations and in other applications. Such compositions and methods may be applied to prevent or reduce or mitigate plugging of annular spaces, pipes, transfer lines, valves, and other places or equipment downhole where hydrocarbon hydrate solids may form under conditions conducive to their formation or agglomeration.

The term "inhibiting" is used herein in a broad and general sense to mean any improvement in preventing, controlling, delaying, reducing or mitigating the formation, growth and/or agglomeration of hydrocarbon hydrates, particularly light hydrocarbon gas hydrates in any manner, including, but not limited to kinetically, thermodynamically, by dissolution, by breaking up, by anti-agglomeration other mechanisms, or any combination thereof. Although the term "inhibiting" is not intended to be restricted to the complete cessation of gas hydrate formation, it may include the possibility that formation of any gas hydrate is entirely prevented.

The terms "formation" or "forming" relating to hydrates are used herein in a broad and general manner to include, but are not limited to, any formation of hydrate solids from water and hydrocarbon(s) or hydrocarbon and non-hydrocarbon gas(es), growth of hydrate solids, agglomeration of hydrates, accumulation of hydrates on surfaces, any deterioration of hydrate solids plugging or other problems in a system and combinations thereof.

The term "low dosage" used with respect to low dosage hydrate inhibitors (LDHIs) as defined herein refers to volumes of less than 5 volume % (vol %) of the aqueous fluids. In some non-limiting embodiments, the vol % for thermodynamic hydrate inhibitors may be considerably higher, which depends on both the system sub-cooling and hold time.

The present apparatus and methods may be useful for inhibiting hydrate formation for many hydrocarbons particularly including hydrocarbon and non-hydrocarbon mixtures. The method is expected to be particularly useful for studying hydrates involving lighter or low-boiling, $C_1$-$C_5$, hydrocarbon gases, non-hydrocarbon gases or gas mixtures at hydrate-forming conditions. Examples of such gases include, but are not necessarily limited to, methane, ethane, ethylene, acetylene, propane, propylene, methylacetylene, n-butane, isobutane, 1-butene, trans-2-butene, cis-2-butene, isobutene, butene mixtures, isopentane, pentenes (including mixtures of pentenes), natural gas, carbon dioxide, hydrogen sulfide, nitrogen, oxygen, argon, krypton, xenon, and mixtures thereof. These molecules are also termed hydrate-forming guest molecules herein. Other examples include various natural gas mixtures that are present in many gas and/or oil formations and natural gas liquids (NGL). The hydrates of all of these low-boiling hydrocarbons are also referred to as gas hydrates. The hydrocarbons may also comprise other compounds including, but not limited to CO, $CO_2$, COS, hydrogen, hydrogen sulfide ($H_2S$), and other compounds commonly found in gas/oil formations or processing plants, either naturally occurring or used in recovering/processing hydrocarbons from the formation or both, and mixtures thereof.

Suitable gas hydrate inhibitors herein may include, but are not necessarily limited to, known gas hydrate inhibitors, in particular LDHIs (in contrast to thermodynamic inhibitors such as salts or glycols), including, but not limited to cationic, anionic, amphoteric, and non-ionic LDHIs. Alternatively, the LDHI may be a kinetic hydrate inhibitor in one non-limiting embodiment, as opposed to anti-agglomerates. Often however, both LDHIs and thermodynamic inhibitors are used together.

In addition to the gas hydrate inhibitor herein, the production fluid inhibitor composition and the completion fluid may further comprise other additional components, including, but not limited to, different controlling or inhibiting chemistries such as corrosion inhibitors, wax inhibitors, scale inhibitors, asphaltene inhibitors and other gas hydrate inhibitors and/or solvents.

Because some of the gas hydrate inhibitor disclosed herein will be solids or gummy-like amorphous organic materials under ambient conditions, it is often helpful to use a suitable solvent as described above in the composition. This allows the formation of a homogeneous or uniform solution, suspension, emulsion or a combination of these, of all the components for easier mixing or distributing or dispersing the composition in the hydrocarbon/water production fluid or system to be treated. As a result, more efficient and/or favorable contacting of the composition with the mixture comprising water and the hydrate-forming guest molecules can be effected. Suitable solvents for gas hydrate inhibitors may include, but are not limited to water; at least one oxygenated compound selected from $C_1$-$C_6$ alcohols, $C_2$-$C_6$ glycols, $C_1$-$C_6$ mono-aliphatic, preferably mono-alkyl, ethers of $C_2$-$C_6$ glycol, glycerin, $C_1$-$C_6$ mono-aliphatic, particularly mono-alkyl, ethers of glycerin, $C_1$-$C_6$ di-aliphatic, particularly dialkyl, ethers of glycerin, glycerin esters of $C_1$-$C_6$ carboxylate; tetrahydrofuran; N-methylpyrrolidone; sulfolane; $C_3$-$C_{10}$ ketones, and mixtures thereof. Examples of acceptable solvents in one non-limiting embodiment include water and liquid oxygenated materials such as methanol, ethanol, propanol, glycols like ethylene glycol, 1,2-propylene glycol, 1,3-propylene glycol, glycerin, esters and ethers of glycerin, CELLOSOLVE® (2-ethoxyethanol), CELLOSOLVE derivatives, 2-propoxyethanol, 2-isopropoxyethanol, 2-butoxyethanol, 2-isobutoxyethanol, 2-methoxyethanol, ethoxylated propylene glycols, ketones such as cyclohexanone and diisobutylketone, and mixtures thereof. The solvent is present in the total hydrocarbon hydrate inhibiting composition in the range of from 0 wt % to about 85 wt %, preferably from about 0 wt % to about 65 wt %, of the total composition, based on volume. CELLOSOLVE is a registered trademark of Union Carbide Corporation.

Many modifications may be made in the apparatus and methods of this invention without departing from the spirit and scope thereof that are defined only in the appended claims. For example, the design of the bench test loop may be different from those explicitly mentioned herein. Various combinations of loop contours, impellers and bits, pigs or balls other than those described here are also expected to be useful. For instance, the pig, ball or bit might be battery powered and self-propelled instead of driven or impelled remotely by an impeller. Further, use of the hydrate inhibition test loops described herein with mixtures of water, hydrocarbons and hydrate-forming guest molecules different from those exemplified herein would be expected to be successful within the context of this invention.

The terms "comprising" and "comprises" as used throughout the claims herein shall be interpreted to mean "including but not limited to".

The test apparatus may consist of or consist essentially of the recited elements. In non-limiting examples, the test apparatus may consist of or consist essentially of a length of hollow pipe forming a loop, a cooler, a pressurizer, at least one pig, and at least one impeller, as defined in the claims.

What is claimed is:

1. A test apparatus for formation of hydrates comprising:
   a length of hollow pipe forming a loop having an interior surface;
   at least one opening in the loop;
   a cooler for cooling a fluid in the loop;
   a pressurizer for pressurizing the fluid in the loop;
   at least one pig within the loop, where the pig is selected from the group of shapes consisting of spheres, eggs, spheres with surface features, eggs with surface features, and combinations thereof, where the surface features are selected from the group consisting of indentations, bumps, passageways, and combinations thereof, where the pig has an exterior surface; and
   at least one impeller adjacent the loop configured to remotely impel the at least one pig to circulate the fluid in the loop,
   where a surface is smooth, the surface being selected from the group consisting of the interior surface of the loop, the exterior surface of the pig, and both so there is an absence of scraping between the pig and the interior surface when the pig is circulated through the loop.

2. The test apparatus of claim 1 where a surface selected from the group consisting of the interior surface of the loop, the exterior surface of the pig, and both has a friction-reducing coating thereon selected from the group consisting of fluorocarbons and silicones.

3. The test apparatus of claim 1 where the loop has an interior diameter and the pig has an exterior diameter, where the exterior diameter of the pig is smaller than the interior diameter of the loop.

4. The test apparatus of claim 2 where a single impeller remotely impels the pig to circulate all loops of the test apparatus.

5. The test apparatus of claim 1 where the loop is circular.

6. The test apparatus of claim 1 where the cooler is configured to reduce a temperature of the fluid to about 30° F. (about −1° C.) or below, and the pressurizer is configured to pressurize the fluid to a pressure of about 1000 psig (about 7 MPa) or above.

7. The test apparatus of claim 1 where the fluid comprises water and hydrate-forming guest molecules that form hydrates at hydrate forming conditions, where the hydrate-forming guest molecules comprise at least one selected from the group consisting of methane, ethane, ethylene, acetylene, propane, propylene, methylacetylene, n-butane, isobutane, 1-butene, trans-2-butene, cis-2-butene, isobutene, butene mixtures, isopentane, pentenes, natural gas, carbon dioxide, hydrogen sulfide, nitrogen, oxygen, argon, krypton, and xenon.

8. The test apparatus of claim 1 where the impeller is a magnet and the pig is formed at least in part of a material responsive to a magnetic field.

9. A multi-test apparatus for the formation of hydrates comprising:
 at least two lengths of hollow pipe each forming a loop, each loop having an interior surface;
 at least one opening in each loop;
 a cooler for cooling a fluid in each loop, where the cooler is configured to reduce a temperature of the fluid to about 30° F. (about −1° C.) or below;
 a pressurizer for pressurizing the fluid in each loop, the where pressurizer is configured to pressurize the fluid to a pressure of about 1000 psig (about 7 MPa) or above;
 at least one pig within each loop, where the at least one pig is formed at least in part of a material responsive to a magnetic field and selected from the group of shapes consisting of spheres, eggs, spheres with surface features, eggs with surface features, and combinations thereof, where the surface features are selected from the group consisting of indentations, bumps, passageways, and combinations thereof, where each pig has an exterior surface; and
 at least one impeller adjacent the loops that is configured to remotely impel the pigs to circulate their respective loops in their respective fluids, where the impeller includes a magnetic source and is configured to impel the pigs to circulate,
where a surface selected from the group consisting of the interior surfaces of the loops, the exterior surfaces of the pigs and both are smooth so there is an absence of scraping between the pig and the interior surface when the pig is circulated through the loop.

10. The multi-test apparatus of claim 9 where a surface selected from the group consisting of the interior surfaces of the loops, the exterior surfaces of the pigs and both have a friction-reducing coating thereon selected from the group consisting of fluorocarbons and silicones.

11. The multi-test apparatus of claim 9 where the loops have an interior diameter and the pigs have an exterior diameter, where the exterior diameter of the pig is smaller than the interior diameter of the respective loop within which the pig circulates.

12. The multi-test apparatus of claim 9 further comprising a single impeller configured to remotely impel the pigs to circulate.

13. The multi-test apparatus of claim 9 where the loops are circular.

14. The multi-test apparatus of claim 9 where the fluid comprises water and hydrate-forming guest molecules that form hydrates at hydrate forming conditions, where the hydrate-forming guest molecule comprises at least one selected from the group consisting of methane, ethane, ethylene, acetylene, propane, propylene, methylacetylene, n-butane, isobutane, 1-butene, trans-2-butene, cis-2-butene, isobutene, butene mixtures, isopentane, pentenes, natural gas, carbon dioxide, hydrogen sulfide, nitrogen, oxygen, argon, krypton, and xenon.

15. A method of testing for formation of hydrates in a test apparatus for the formation of hydrates comprising:
 using the test apparatus to test for formation of hydrates, the test apparatus comprising:
  a length of hollow pipe forming a loop having an interior surface;
  at least one opening in the loop;
  a cooler for cooling a fluid in the loop;
  a pressurizer for pressurizing the fluid in the loop;
  at least one pig within the loop, where the pig is selected from the group of shapes consisting of spheres, eggs, spheres with surface features, eggs with surface features, and combinations thereof, where the surface features are selected from the group consisting of indentations, bumps, passageways, and combinations thereof, where the pig has an exterior surface; and
  at least one impeller adjacent the loop that remotely impels the pig to circulate the loop in the fluid,
  where a surface selected from the group consisting of the interior surface of the loop, the exterior surface of the pig and both is smooth: and
 circulating the pig through the loop using the impeller where there is an absence of scraping between the pig and the interior surface.

16. The method of claim 15, further comprising:
 introducing a fluid into the loop through the opening, where the fluid comprises water and hydrate-forming guest molecules that form hydrates at hydrate forming conditions;
 cooling the fluid to a temperature of about 30° F. (about −1° C.) or below and pressurizing the fluid to a pressure of about 1000 psig (about 7 MPa) or above to create hydrate forming conditions;
 and
 monitoring the fluid for hydrate formation.

17. The method of claim 15 where a surface selected from the group consisting of the interior surface of the loop, the exterior surface of the pig, and both has a friction-reducing coating thereon selected from the group consisting of fluorocarbons and silicones.

18. The method of claim 15 where the loop has an interior diameter and the pig has an exterior diameter, where the exterior diameter of the pig is smaller than the interior diameter of the loop.

19. The method of claim 15 where the loop is circular.

20. The method of claim 16 where the hydrate-forming guest molecule comprises at least one selected from the group consisting of methane, ethane, ethylene, acetylene, propane, propylene, methylacetylene, n-butane, isobutane, 1-butene, trans-2-butene, cis-2-butene, isobutene, butene mixtures, isopentane, pentenes, natural gas, carbon dioxide, hydrogen sulfide, nitrogen, oxygen, argon, krypton, and xenon.

21. The method of claim 16 where the fluid further comprises a hydrate inhibitor.

22. The method of claim 15 where the at least one impeller is a magnet and the pig is formed at least in part of a material responsive to a magnetic field, and where the impeller is configured to of impel the pig to circulate.

* * * * *